United States Patent [19]

Childress et al.

[11] Patent Number: 4,685,925
[45] Date of Patent: Aug. 11, 1987

[54] VOLUNTARY OPENING PREHENSION DEVICE

[75] Inventors: Dudley Childress, Wilmette; John Strysik, Chicago, both of Ill.

[73] Assignee: Northwestern University, Evanston, Ill.

[21] Appl. No.: 663,154

[22] Filed: Oct. 22, 1984

[51] Int. Cl.$^4$ .............................................. A61F 1/06
[52] U.S. Cl. ..................................................... 623/25
[58] Field of Search ........................ 3/12, 1.1; 623/25

[56] References Cited

U.S. PATENT DOCUMENTS

| | | |
|---|---|---|
| 3,501,776 | 3/1970 | Beeker et al. |
| 3,557,387 | 1/1971 | Ohlenbusch et al. ................... 3/1.1 |
| 3,641,993 | 2/1972 | Gaarder et al. |
| 3,883,900 | 5/1975 | Jerard et al. .......................... 623/25 |
| 4,067,070 | 1/1978 | Seamone et al. ....................... 3/1.1 |
| 4,158,196 | 6/1979 | Crawford, Sr. ........................ 3/1.1 |
| 4,246,661 | 1/1981 | Pinson .................................. 623/25 |
| 4,285,345 | 8/1981 | Mensink et al. |
| 4,291,421 | 9/1981 | Massey et al. .......................... 3/12 |

OTHER PUBLICATIONS

"Atlas of Limb Prosthetics" p. 149, Jul. 16, 1981.
"Proceedings of the Fourth International Symposium of External Control of Human Extremities", Dubrovnik, 1972.
"Myoelectric Controlled Hand Prosthesis in Children", Sorbye, *Int. J. Rehab. Res.* 1:15–25, 1977.
"EMG Operated Electronically Artificial Leg Controller", Sexena, published in *Medical and Biological Engineering and Computer,* Sep., 1977.

*Primary Examiner*—Leo P. Picard
*Attorney, Agent, or Firm*—Welsh & Katz, Ltd.

[57] ABSTRACT

A voluntary opening prehension device is constructed with a pivot member having a pair of fingers mounted thereon and extending distally from the pivot member. The fingers may be pivoted individually or simultaneously so as to selectively separate or converge at their distal ends. An electric motor is used to separate the fingers. A closing mechanism biases the fingers into contact with each other when the motor is not in operation. A battery supplies electrical power to the motor. A field effect transistor driver serves as a switch for actuating the electric motor when it is supplied with a myopulse of a specified threshold strength or greater. This reduces the amount of electrical power utilized to operate the device since the motor is actuated only when a clear signal is sent from the user. A control mechanism supplies the myopulse to the field effect transistor driver in response to a myoelectric signal generated by the user.

26 Claims, 8 Drawing Figures

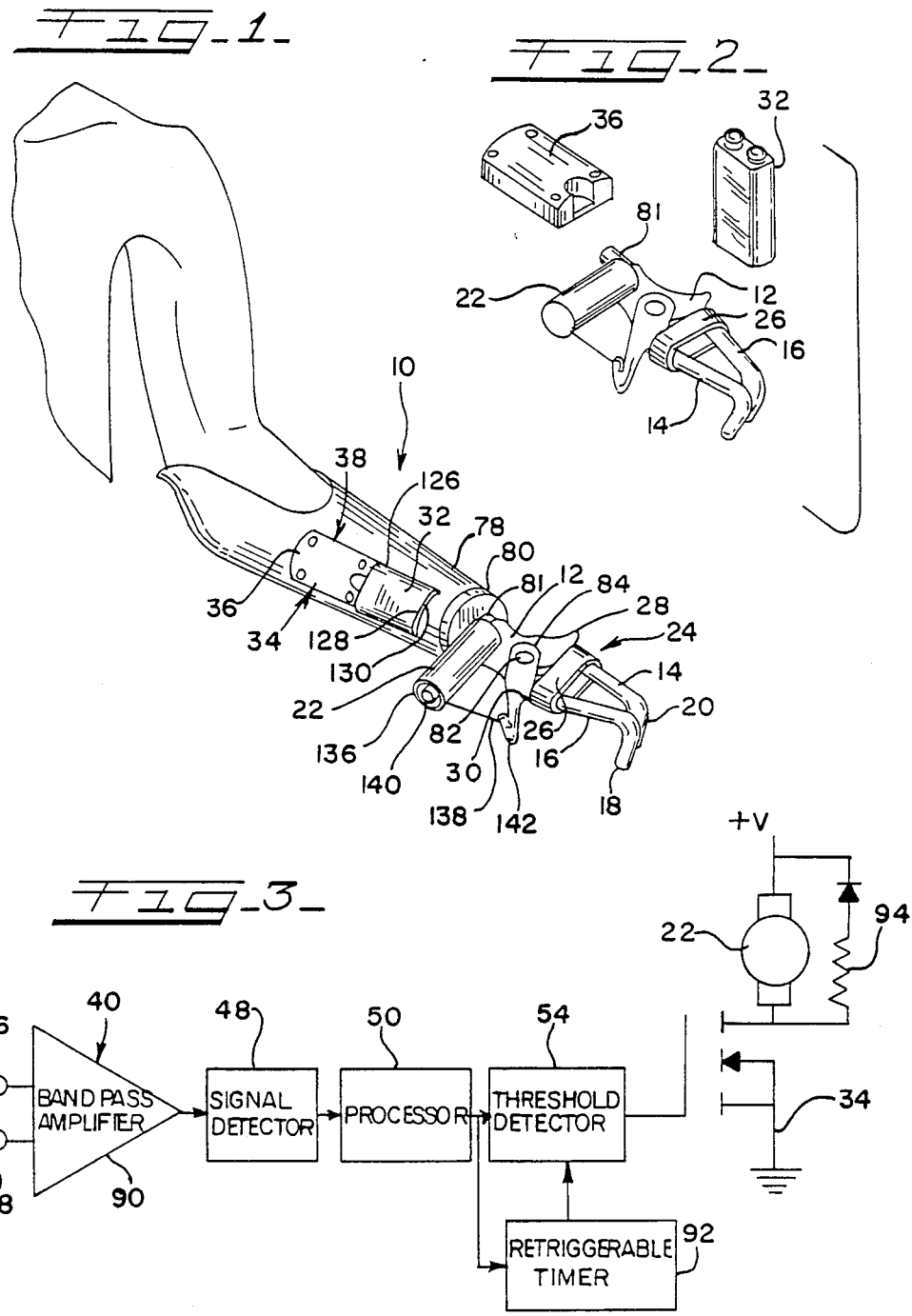

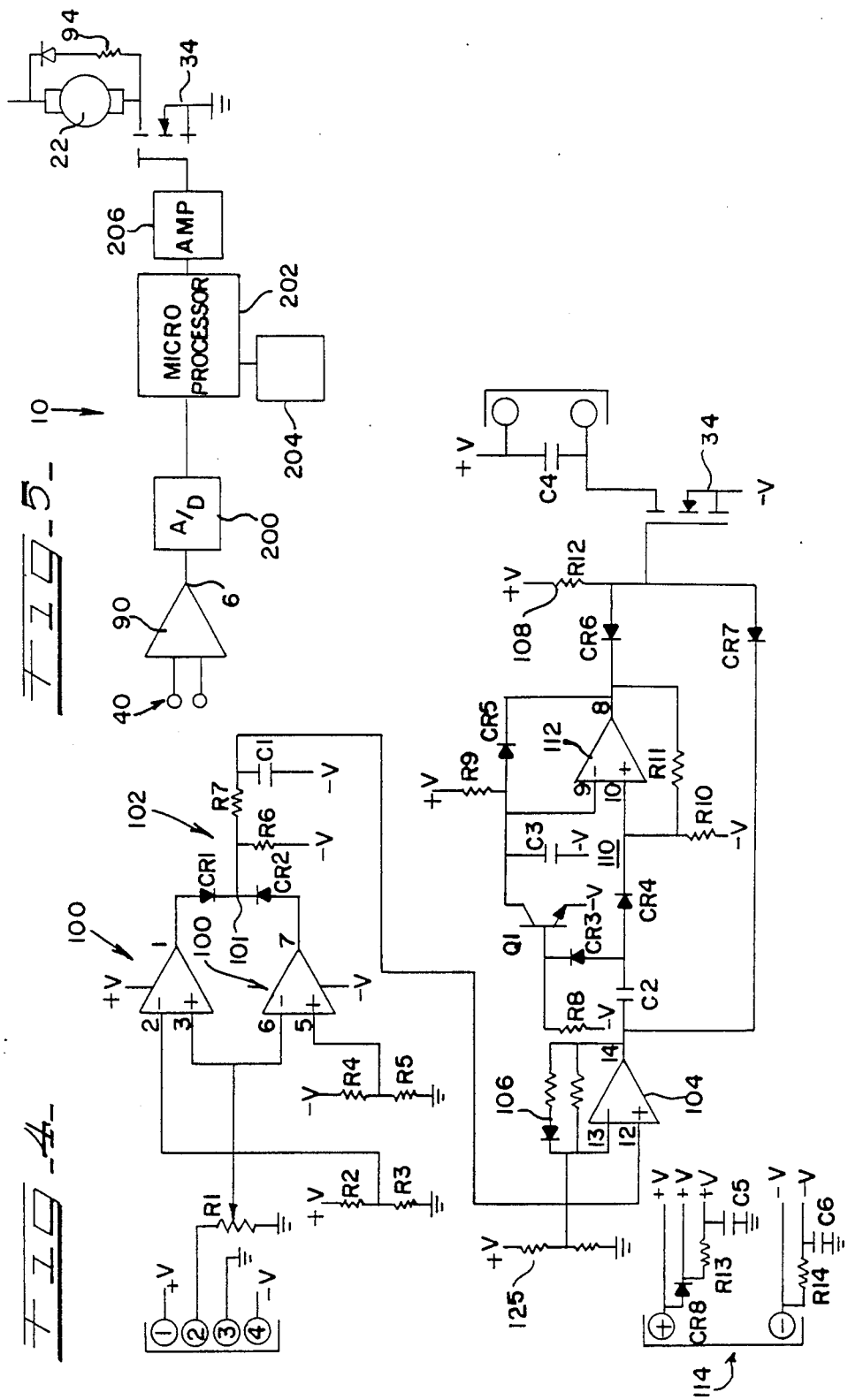

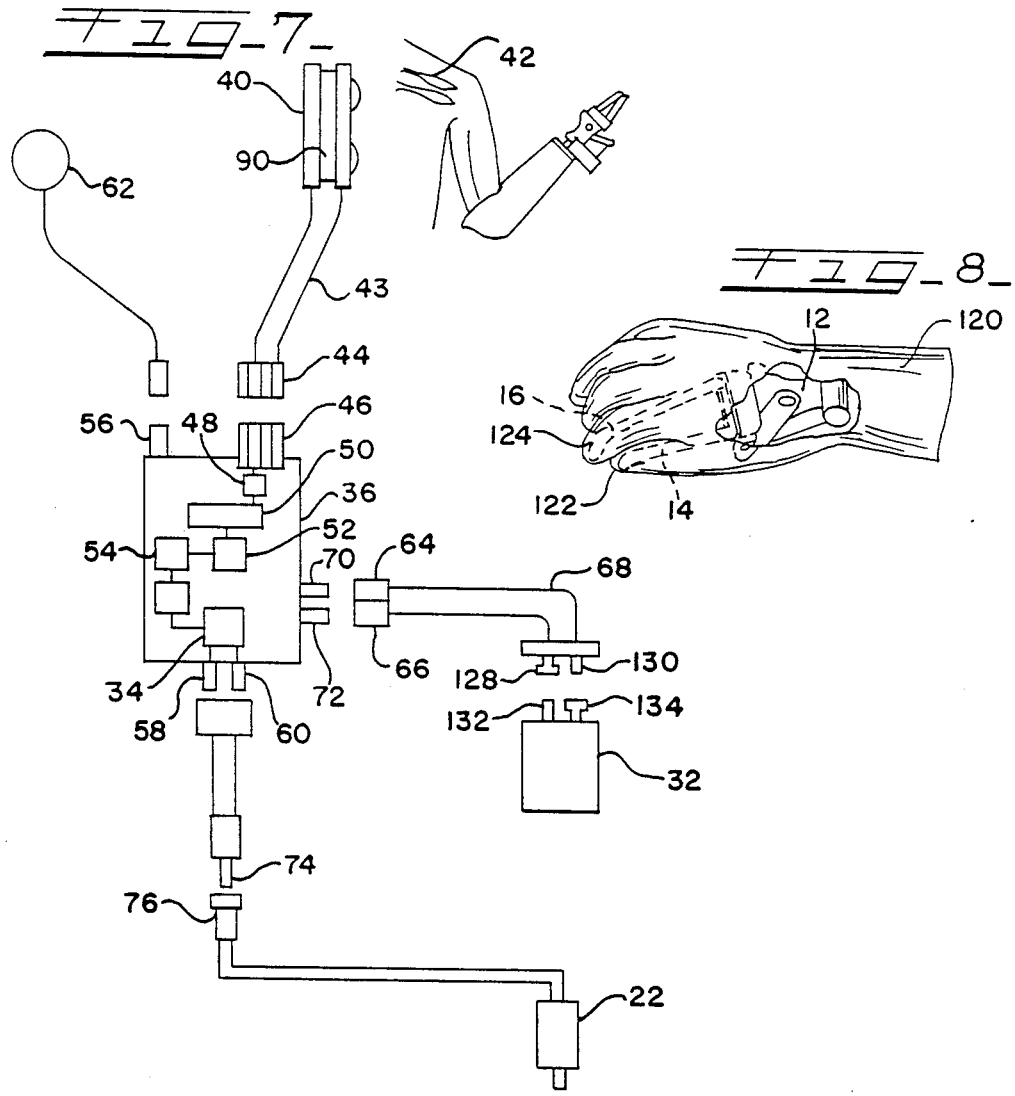
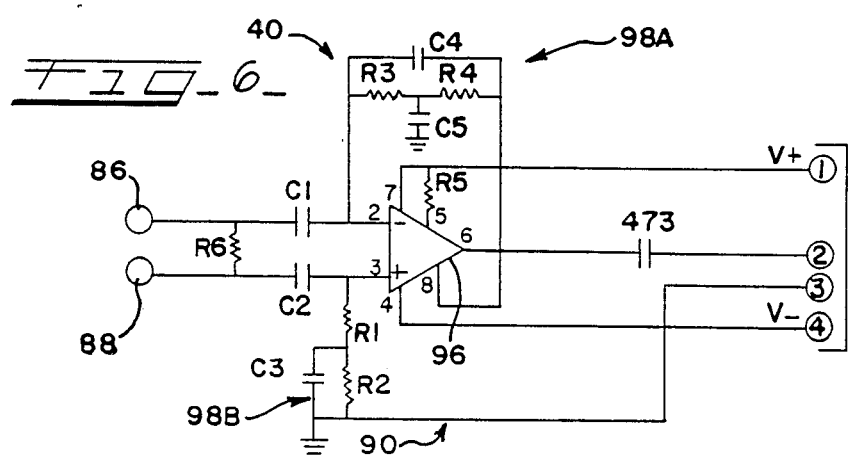

VOLUNTARY OPENING PREHENSION DEVICE

BACKGROUND OF THE INVENTION

The U.S. Government has rights in this invention pursuant to funding under grant V101 (93) p-879 from the Veteran's Administration.

The present invention relates generally to prosthetic devices and in particular to myoelectrically controlled hook/hand systems for amputees.

In 1972, the first electrically powered hook utilizing synergetic prehension was constructed by D. S. Childress (Proceedings of the Fourth International Symposium of External Control of Human Extremities, Dubrovnik, 1972). Sorbye, Myoelectric Controlled Hand Prosthesis in Children, Int. J. Rehab. Res. 1:15–25, 1977 has shown the efficacy of fitting myoelectric hands to below-elbow-limb-deficient children and his work has led to the development of the "Swedish Hand", a small electric hand made by SystemTeknik and controlled by Otto Bock Electronics.

The use of bipolar transistors in myoelectric devices may be seen in U.S. Pat. Nos. 3,883,900 3,641,993, 3,501,776 and the article "EMG Operated Electronically Artificial Leg Controller" by Sexena published in *Medical and Biological Engineering and Computer*, September, 1977. However, the prior art does not reveal the use of field effect transistors in artificial limb type prosthetic devices.

The use of local field effect transistors in implanted devices, such as pacemakers, may be seen in U.S. Pat. No. 4,285,345. However, the current requirements from a pacemaker are vastly different than than of an artificial prosthetic device in which a pair of fingers must be separated by an electric motor and operated with sufficient torque to grasp an object firmly, in an artificial hand, or move body weight in the case of an artificial leg. Thus the present design for a field effect transistor driver utilized in a myoelectrically controlled hook/hand device represents a non-obvious improvement over the prior art.

BRIEF SUMMARY OF THE INVENTION

A voluntary opening prehension device is provided in the present invention which includes a pivot member having a pair of fingers extending distally therefrom. The fingers are pivotally mounted on the pivot member so as to be selectively separated or converged together at their distal ends. An electric motor is used for effecting the selective separation of the finger members. A closing mechanism such as a rubber band is used for biasing the finger members in contact with each other. The rubber elastic band is wrapped around the two fingers so as to resiliently retain them in contact with each other. The rubber band is sufficiently elastic to allow the fingers to open, but when the electric motor is inactivated the rubber band returns the fingers to a closed position.

A battery is used to supply the electrical power to the electric motor. Interposed between the battery and the electric motor is a field effect transistor driver which actuates the electric motor when it is supplied with an electric signal of a specified threshold strength. As a result of the use of the field effect transistor driver, the efficiency of the power driver to operate the device is much greater than with a conventional bipolar transistor. A myoelectric control mechanism is used for supplying an electric control signal to the field effect transistor driver in response to a myoelectric signal generated by the user.

The previously mentioned control mechanism preferably comprises a pair of electrodes affixed to the skin near a voluntary muscle of the user. A myoelectric signal is generated by the user at the electrodes. A complementary metal oxide semiconductor amplifier amplifies the myoelectric signal from the electrodes. A signal detector then detects the myoelectric signal and generates what is called a myopulse, which after smoothing by the processor suitable for actuating the field effect transistor driver. A threshold detector restricts the generation of a myopulse from the processor to those instances in which the myoelectric signal is of a specified minimum voltage strength or less.

In an alternative embodiment, the control mechanism may utilize a transducer rather than an electrode for physically sensing movement of a voluntary muscle and transforming said movement into an electrical signal. Similarly, although the present invention is designed primarily for artificial hands, other prosthetic devices such as artificial legs or arms may also utilize a field effect transistor driver. The same savings in electric power and consequent extension of the life of the battery may be thereby provided.

In one embodiment the field effect transistor driver, the signal detector, the processor and the threshold detector are affixed to a module which is selectively removable from and connectable to the voluntary opening prehension device. This allows easy repair or replacement of components as required. In addition, the battery is also selectively removable from and connectable to the voluntary opening prehension device. A quick disconnect is provided for this purpose. The battery may thereby be recharged or replaced as desired.

As is evident from the previous paragraphs, the voluntary opening prehension device of the present invention is used as an artificial hand. The artificial hand further includes a socket which allows selective attachment or removal of the the pivot member from an artificial forearm. In one embodiment a thermoplastic covering encompasses the previously mentioned finger members and pivot and is formed in the shape of a hand so as to simulate the appearance and function of a natural hand. A second pivot member may also be provided having fingers extending therefrom, so that the user may select between an artificial hand having a thermoplastic covering or one which does not.

In a preferred embodiment, the artificial hand previously described further includes a retriggerable timer which limits actuation of the electric motor to a select time period. As a result power consumption is reduced in utilizing the artificial hand. A preferred time period is four seconds, which allows the fingers of the hand to be opened and placed around an object, whereupon the closing mechanism biases the fingers back towards a closed position, causing them to grip the object which is positioned between the tips of the two fingers.

The field effect transistor driver preferably comprises a vertical metal oxide semiconductor transistor having a voltage drop of 40 to 70 millivolts when driving the electric motor. The vertical metal oxide semiconductor transistor reduces the amount of voltage drop required when driving the electric motor, in comparison to traditional bipolar transistors. Similarly, the amplifier previously mentioned preferably comprises a complementary metal oxide semiconductor bandpass amplifier which also has a low current requirement.

In the embodiment described the prosthetic device utilizes a quiescent current of 18 microamperes or less. In order to improve the operation of the device, a smoothing circuit is electrically connected to the threshold detector which removes fluctuations in output voltage. A buffer circuit is positioned between the signal detector and the electric motor which isolates the signal detector and electrically turns on the FET Drive to the electric motor. The battery, in a preferred embodiment comprises a 9-volt transistor battery, which is low in cost, provides a reliable sustained power and is easy to replace. The battery is contained within an easy access battery chamber in the artificial forearm of the device for removal and replacement as desired. The battery powers the electric motor, which pivots the finger members either by means of a pulley or a gear drive. In the case of a pulley, a cable is connected from the shaft of the electric motor to one of the finger members. When the electric motor is actuated the finger member is thereby pivoted away from the other finger member so as to open the space between the distal ends of the finger members. When the electric motor is deactivated the closing mechanism returns the finger members to a contact position at their distal end.

BRIEF DESCRIPTION OF THE DRAWINGS

FIG. 1 of the drawings is a front perspective view of a voluntary opening prehension device.

FIG. 2 of the drawings is an exploded view of the hook portion, the battery portion and the control circuitry of the voluntary opening prehension device of FIG. 1.

FIG. 3 of the drawings is a block diagram of the electric circuitry employed in the voluntary opening prehension device of FIG. 1.

FIG. 4 of the drawings is a schematic electrical diagram of one embodiment of the circuitry that may be employed in the voluntary opening prehension device of Figure 1.

FIG. 5 of the drawings is a block diagram of an alternative embodiment of the circuitry employed in the voluntary opening prehension device of FIG. 1.

FIG. 6 of the drawings is a schematic diagram of the electrical circuitry for an electrode adapted for use with the voluntary opening prehension device of FIG. 1.

FIG. 7 of the drawings is a schematic diagram of the voluntary opening prehension device of FIG. 1, showing in particular attachment of an electrode to a voluntary muscle of the patient, a battery selectively separable from a myoprocessor circuit, and a motor selectively attachable to the myoprocessor circuit.

FIG. 8 of the drawings is a top view of the voluntary opening prehension device of FIG. 1 encased in an thermoplastic sheath which is formed in the shape of a hand.

DETAILED DESCRIPTION OF THE PREFERRED EMBODIMENT

Referring now to the drawings and in particular to FIG. 1, a voluntary opening prehension device 10 is shown. Voluntary opening prehension device 10 is an artificial hand, which opens in response to a myoelectric signal from the patient, remains open until released by the user or for a specified period of time and closes upon the object to be grasped.

Voluntary opening prehension device 10 comprises a pivot member 12 having a pair of fingers 14 and 16 extending distally therefrom. In the embodiment shown in FIG. 1 finger 16 is pivotally mounted on pivot 12, whereas finger 14 is fixedly positioned thereon. When finger 16 is pivoted, distal end 18 of finger 16 is separated from distal end 20 of finger 14. Alternatively, distal ends 18 and 20 may be converged together when desired.

Electric motor mechanism 22 is used for selectively separating fingers 14 and 16. Specifically, electric motor 22, is used to pivot finger 16 so as to cause separation of distal ends 18 and 20. Closing mechanism 24 biases distal ends 18 and 20 into contact with each other. In the embodiment shown closing mechanism 24 comprises an elastic band 26 circumscribing the middle portions 28 and 30 of fingers 14 and 16, respectively. Elastic band 26 tends to hold fingers 14 and 16 together, but allows them to be pivoted apart by means of electric motor mechanism 22. A battery 32 is electrically connected to electric motor mechanism 22 by means of wires 68 (as seen in FIG. 7). Battery 32 supplies electrical power to electric motor 22. A field effect transistor driver 34, which is attached to circuit board 36 is used for actuating electric motor mechanism 22. By this it is meant that an electric signal is sent from field effect transistor driver 34 to electric motor 22, causing the motor 22 to move finger 16. Field effect transistor driver 34 also serves, at least in part, to limit actuation of electric motor 22 to those instances when a signal of a specified threshold strength or greater is received from control mechanism 38. Field effect transistor driver 34 and control mechanism 38 are also located on circuit board 36. Thus control mechanism 38 receives a myoelectric signal from the patient and translates it into a myoelectric pulse which in turn actuates electric motor mechanism 22.

The control mechanism 38 incorporated in voluntary opening prehension device 10 includes an electrode 40 which is best seen in FIG. 7 of the drawings. Electrode 40 is affixed to the user proximate a voluntary muscle 42. Electrode 40 contains amplifier 90. In the illustration shown the voluntary muscle 42 used is in the shoulder latissimus dorsi. However, voluntary muscles in the forearm or upper arm may also be used in order to more closely simulate normal functioning of the hand. Electrode 40 is connected by means of wires 43 to a coupling 44 which in turn is connected to coupling 46 on circuit board 36. Coupling 46 in turn is connected to signal detector 48 which detects the myoelectric signal from electrode member 40, as will be discussed in greater detail herein. The signal from the detector then generates a myopulse which is sent electronically to processor 50, which smoothes the signal, making it suitable for actuating field effect transistor driver 34. A threshold detector 54 is interposed between processor 50 in FIG. 3, and field effect transistor driver 34. Threshold filter 54 restricts generation of a myopulse to those instances in which the myoelectric signal from electrode 40 is of a specified minimum strength or greater. As a result, only when definite, strong voluntary muscle movement from voluntary muscle 42 is detected by electrode 40 is electric motor 22 actuated, so as to separate fingers 14 and 16.

As further seen in FIG. 7, field effect transistor driver 34, and processor filter 50, are all fixed to circuit board 36 which in turn is modular so as to be removable from voluntary opening prehension device 10. By modular it is meant that the components are connected to circuit board 36 by means of quick release plugs such as plugs 46, 56, 58 and 60. It should be noted in this regard that plug 56 is connected to plug 57 which in turn is connected to ground 62 so as to serve as a reference. Battery 32 is also connected by means of plugs 64 and 66 and wires 68 to corresponding plugs 70 and 72 on circuit board 36. Thus battery member 32 is also selectively removable and replaceable from voluntary opening prehension device 10. It may be further seen in FIG. 7 that circuit board 36 with the aforesaid components is connected to electric motor 22 by means of quick release plugs 74 and 76. In a preferred embodiment quick release plugs 74 and 76 are positioned at the juncture between pivot 12 and forearm member 78. Thus quick, easy and low-cost disconnection or connection of pivot member 28 is provided.

The aforesaid artificial forearm member 78, as may be seen in FIG. 1, is attached to the arm of the patient. Preferably artificial forearm member 78 is formed as a plastic housing which contains the aforesaid circuit board 36, and battery 32. Forearm 78 may be constructed of a variety of plastic, metallic, or natural materials, as is commonly known in the art.

Pivot member 12 is attached to the distal end 80 of artificial forearm member 78 at socket 81. As indicated previously, the electrical connection between forearm member 78 and pivot 12 is accomplished by means of plugs 74 and 76. Pivot member 12 may thus be snap locked onto artificial forearm 78 or alternatively threadedly connected thereto.

As further seen in FIG. 1, finger member 14 is fixedly attached to pivot member 12, while finger 16 is pivotally mounted on pivot member 12. By pivotally mounted, it is meant that finger 16 is attached to pivot 12 by means of a pin 82 extending through the proximal end 84 of finger 16 and into and through pivot member 12. Either pin 82 may be pivoted in pivot 12, or finger 16 may be pivotable on pin 82. Thus pivoting of a finger 16 is effective to separate or bring together distal ends 18 and 20 of fingers 14 and 16.

Turning now to FIG. 3 of the drawings, another schematic diagram of voluntary opening prehension device 10 may be seen. Electrode 40 comprises contact points 86 and 88 which are attached to the patient near a voluntary muscle. The contraction of the muscle generates a myoelectric signal which changes the differential signal between the two electrodes. The signal is amplified by bandpass amplifier 90. The signal from bandpass amplifier 90 is detected by signal detector 48. A myopulse from signal detector 48 is in turn processed by processor 50, the myopulse being above or below the threshold level. Threshold detector 54 may also be set at the same threshold or at a different threshold level in order to limit the number of instances in which the motor is actuated. A retriggerable timer 92 is also connected to the device so that after the electric motor 22 has been actuated for a specified period, such as four seconds, the motor is deactivated in order to conserve electrical power. The myopulse in turn actuates the field effect transistor 34, which actuates the motor 22, causing fingers 14 and 16 to separate. Damper 94 keeps finger 14 from closing too rapidly when motor 22 is deactivated.

As may be seen in FIG. 5 of the drawings, in an alternative embodiment the circuitry for voluntary opening prehension device 10 may comprise myotrode 40 containing bandpass amplifier 90 as previously described. An analog to digital converter 200 is connected to pin 6 of bandpass amplifier 90. Connected to analog to digital converter 200 is a low power microprocessor 202 (e.g. Zilog Z.80L) having a memory portion 204 which stores a program. The program instructs the microprocessor to activate field effect transistor 34 when the myoelectric signal from bandpass amplifier 90 is of sufficient strength. The analog to digital converter converts the analog signal from bandpass amplifier 90 into a digital signal called a myopulse which is coupled to an input port of the microprocessor as shown. The digital signal is read by the microprocessor 202 and processed by the microprocessor 202 under control of the program stored in memory 204. The program then instructs the microprocessor 202 to send an activation signal to the field effect transistor 34 which in turn actuates field effect transistor 34. The activation signal may be coupled through an optional buffer amplifier 206. Field effect transistor 34 in turn actuates electric motor 22. Microprocessor 202 is further instructed by a program in memory 204 to deactuate field effect transistor 34 when the myoelectric signal diminishes or after a selective period of time; in a preferred embodiment four seconds.

Turning now to FIG. 6 of the drawings, when voluntary muscle 42 is flexed, a myoelectric signal is detected between electrodes 86 and 88; for example, when a 100 microvolts RMS signal is generated by voluntary muscle 42 of the user, electrode 40 produces a resulting output of 1 volt RMS. This is accomplished by operational amplifier 96, which in a preferred embodiment is an RCA, CA-3078 integrated circuit. Operational amplifier 96 is preferably a complementary metal oxide semiconductor which amplifies the myoelectric signals. Contacts 86 and 88 are capacitively connected by means of RC Network C1, C2 and R6. Capacitors C1 and C2 are preferably Johansen No. 500R15W103KP. Resistor R6 is preferably a Mepco No. 9C-1206-3-A-1003-J-K-R. Connected to operational amplifier 96 is a Bridge-T Network 98, having two legs, 98A and 98B. The first leg 98A is identified as having capacitor C4 and the second leg is identified as having capacitor C3. Capacitors C3 and C4 are Johansen No. 500R15N102JP's. First leg 98A is the feedback element of the operational amplifier 96. The function of second leg 98B is basically to balance operational amplifier 96. Operational amplifier is capacitively coupled with the electrodes 86 and 88 and it is also capacitively coupled with the output. Resistor R5 sets the quiescent current for the operational amplifier 96. Instead of feeding back from the output of operational amplifier 96, the system feeds back through network 98 from the compensation terminal. As a result, amplifier 98 is more stable and has higher gain than can be obtained otherwise.

The output from electrode 40 is passed through variable resistor R1 shown in FIG. 4, which acts as a potentiometer. Resistor R1 serves as a gain control. The signal from variable resistor R1 is divided and fed into dual comparator 100, as shown. The signal that comes out of the potentiometer R1 is an AC signal that fluctuates between positive and negative; it is an amplified myoelectric signal with a mean of zero. Dual comparator 100 comprises two CMOS amplifiers; a ICL 7642 is the preferred integrated circuit. Each of the amplifiers has a separate threshold; one is a positive threshold and one is a negative threshold. The positive threshold is determined by the divider network R2R3 and the negative threshold is determined by the divider network R4R5.

The two thresholds go into the dual comparator 100 at pins 5 and 2. The signal from the variable resistor is fed into pins 3 and 6. When the input myoelectric signal is more positive than the positive threshold, the output voltage of pin 1 goes positive. The output of the dual comparator 100 is normally negative. Thus, when the threshold is exceeded, the output 101 of the comparator 100 goes positive. If the negative threshold is exceeded, pin 7 goes positive. Thus, any time the absolute magnitude of the signal is greater than these thresholds a positive pulse is generated at the output 101. This is called myopulse modulation. The thresholds are set quite low; preferably 30 to 40 millivolts. The signal fed out of the dual comparator 100 is smoothed by an RC network 102. RC network 102 comprises resistors R6 and R7, and capacitor C1. The resulting signal is positive.

The signal from RC network 102 is then fed into a second comparator 104. However, comparator 104 is incorporated in a circuit which includes a hysteresis circuit 106. The threshold value of the comparator 104 is determined by voltage divider 125. Connected to comparator 104 is hysteresis network 106 which comprises a set of two resistors and a diode which prevent the device from cycling on and off due to the fluctuations in voltage of the signal when it is near threshold level. Again, amplifier 104 is preferably a ICL 7642; a complementary metal oxide semiconductor circuit fabricated into an integrated circuit. As a result of the positive condition of the output of the amplifier 104, field effect transistor driver 34 turns on. Transistor 34, which is a VNO300 or an BUZ 71A, delivers a current to electric motor 22. Electric motor 22 then moves finger 16 so as to separate fingertips 18 and 20 thereby allowing the patient to place fingertips 18 and 20 around an object. Diodes CR6 and CR7 both have to be backward biased in order for field effect transistor driver 34 to turn on. Thus, when the output of comparator 104 goes positive, the positive signal is coupled to the transistor 34 through the diode CR7, and to the input of operational amplifier 112 through the capacitor C2 and diode CR4. This positive signal applied to the operational amplifier 112 causes the output (i. e. pin 8) to go positive. Diodes CR6 and CR7 are now back biased, resulting in activation of the transistor 34. After a period of time determined by the RC network formed by resistor R9 and capacitor C3 (four seconds in the preferred embodiment), the output of amplifier 112 will go negative. This turns field effect transistor driver 34 off so that the battery is not run down. The reason for this is so that if the device is placed on a child, the child will not be able to run the battery down. Timer 110 is reset when it times out or whenever a positive signal is again coupled through C2 and CR4. RC network R9C3 is actuated by a transistor Q1 which is preferably an MPS6514. The actuation of transistor Q1 discharges capacitor C3 which resets the timing element. Timer 110 is basically a one-shot retriggerable monostable multivibrator.

In the bottom left hand portion of FIG. 4 may be seen decoupling circuitry 114 for the battery 32. Basically the decoupling circuitry 114 comprises an RC decoupling network consisting of resistor R14, capacitor C6, resistor R13 and capacitor C5 along with diode CR8. Again, diode CR8 is a 1N914. The RC decoupling network 114 lessens high frequency fluctuations in the power supply voltages that supply the amplifier and thresholds. As a result, the thresholds previously mentioned are maintained at a relatively constant level. When motor 32 is turned o it draws current from the battery that pulls the voltage on the battery down. Since it is undesirable to have thresholds drop, the RC decoupling network 114 prevents this. Diode CR8 protects the circuitry in the event the battery is put in backwards. RC decoupling network 114 also supplies the electrical current to myotrode 40 shown in FIG. 6.

The following list of components summarize the elements of the circuit diagram shown in FIG. 4;

Integrated Circuits 100, 104, 112-NU-2 ICL 7642ECPD

Transistors

Q1-MPS 6514
34—VN 0300 or BUZ 71A

Diodes

CR1 through CR8—1N914

Capacitors

C1—0.001 Centralab #15C103M
C2—0.001 Centralab #15C102M
C3—0.33 Sprague #196D334X9035AH1
C4—0.1 Centralab #20C104M
C5—0.1 Centralab #20C104M
C6—0.1 Centralab #20C104M Resistors ⅛ W 5%

R1—1M Pot Bournes #3339P-1-105
R2—1M
R3—6.8K
R4—1M
R5—6.8K
R6—1M
R7—10M
R8—10M
R9—10M
R10—10M
R11—4.7M
R12—470K
R13—22K
R14—22K Misc.

(4) Connectors Ansley #741
(6) Connectors RN #WTS-36R-1-TG Board NU-110C

In a preferred embodiment, field effect transistor driver 34 comprises an VNO 300M field effect transistor manufactured by Siliconix, Santa Clara, Calif., which features high speed, high peak current switching, direct interfacing to CMOS logic, and inherent protection from thermal runaway. Maximum continuous drain current is 0.7 amps. Peak drain current is 3 amps. Operating temperature range is from minus 55 to 150 degrees centigrade.

In a preferred embodiment, a Micromotor Electronics, Inc., DC micromotor 2233 is utilized as electric motor 22 for separating fingers 14 and 16. Micromotor 2233 requires a supply voltage of 4.5 volts. Maximum output power is 3.89 watts. The no load speed is 8000 RPM plus or minus 12%. Stall torque is 2.61 ounces per inch and the torque constant is 0.757 ounces per inch per amp. A series 22/2 gearhead, manufactured by Micromotor Electronics, Inc., is utilized in connection with the 2233 F micromotor.

Turning to FIG. 8 of the drawings, as previously mentioned, a pivot member 12 may be connected to forearm member 78 by means of a socket 80. In one embodiment of the invention, as seen in FIG. 8, pivot member 12 may be covered with a resilient thermoplastic covering 120 formed in the shape of a human hand. Thermoplastic covering 120 is sufficiently elastic to serve as a closing means 24 for fingers 14 and 16 without the use of elastic band 26. Thermoplastic covering 120 may be constructed of a variety of thermoplastic materials such as PVC or other materials which simulate the appearance and function of a natural hand. By this it is meant that the required resiliency and smoothness and color are provided. As a result, the objects may be picked up between the simulated thumb 122 and index finger 124 of the thermoplastic covering 120. As a result, the user may select between pivot member as shown in FIG. 1 or a pivot member having thermoplastic covering 120 attached thereto.

As previously mentioned, a voluntary open prehension device may be described as a myoelectrically controlled prosthesis. Alternatively, it may be called an artificial hand. However, the use of field effect transistors for artificial prostheses is not limited by the present disclosure of the preferred embodiment only.

Returning to FIG. 1 of the drawings, as previously mentioned, battery member 32 is selectively removable from voluntary opening prehension device 10. In the embodiment shown, battery 32 comprises a 9 volt transistor battery which is inserted into and attached to a easy access battery chamber 126. Contained within battery chamber 126 are contact points 128 and 130, also seen in FIG. 7. Contact points 128 and 130 correspond to, on FIG. 4, power supply voltage + and −. They are connected by means of conventional terminals 132 and 134 on battery 32 to supply electrical power to voluntary opening prehension device 10.

As further seen in FIGS. 1 and 2 of the drawings, electrical motor means 22 preferably comprises a direct current micromotor electrically connected to battery member 22. Micromotor 22 has a linear shaft 136 contained therein and extending perpendicularly therefrom. A cable member 138 is connected to linear shaft 136 at a first end 140 and is attached to finger 16 at a second end 142. As a result, when electric motor 22 is actuated, cable 138 is pulled towards motor 22 thereby pivoting finger 16 on pin 82. Motor 22 pulls cable 138 by means of rotation of shaft 136 so that cable 138 is wound about shaft 136. When fingers 14 and 16 are separated a designated distance, motor shaft 136 ceases to rotate, as a result of the previously mentioned gearhead 22/2. However, when current is no longer supplied to electric motor 22, gearhead 22/2 releases, thereby allowing cable 138 to unwind and finger 16 to return to its original position. This return is effected by means of elastic band 26, which causes fingers 14 and 16 to resiliently return together.

Alternatively, electric motor 22 may be connected to fingers 14 and 16 by means of a gearing mechanism, (not shown) which directly pivots finger 16, or fingers 14 and 16 as desired. However, due to the cost of such a gearing mechanism, the previously mentioned motor and cable is preferred.

The foregoing description and drawings merely explain and illustrate the invention and the invention is not so limited thereto except insofar as those who have the disclosure before them will be able to make modifications and variations therein without departing from the scope of the invention.

What is claimed is:

1. A voluntary opening prehension device comprising:
   a pivot member;
   a pair of finger members extending distally from said pivot member, at least one of said finger members being pivotally mounted thereon for selective separation and convergence of said finger members at their respective distal ends;
   electric motor means for effecting said selective separation of said finger members;
   closing means for biasing at least a portion of said finger members in contact with each other;
   a battery member for supplying electrical power to said electric motor means;
   field effect transistor driver means for actuating said electric motor means when supplied with a myopulse signal of a specified threshold strength or greater, so as to reduce the electric power necessary to operate said prehension device;
   control means for supplying a myopulse to said field effect transistor driver in response to a myoelectric signal generated by the user;
   said control means comprising a signal detector for detecting a myoelectric signal generated by the user;
   a processor for processing said myoelectric signal into a myopulse which is directed to said field effect transistor driver for actuating said driver; and
   a threshold detector for restricting actuating of said motor to those instances in which said myoelectric signal is of a specified minimum voltage strength or greater.

2. The voluntary opening prehension device as described in claim 1 wherein said field effect transistor driver means, said signal detector, said processor and said threshold detector are affixed to a module selectively removable from and connectable to said voluntary opening prehension device, for repair or replacement as desired.

3. The voluntary opening prehension device as described in claim 1 wherein said battery member is selectively removable from and connectable to the voluntary opening prehension device for recharging or replacement as desired.

4. The voluntary opening prehension device of claim 1 wherein a first one of said pair of finger members is fixedly attached to said pivot member and a second one of said pair of finger members is pivotally mounted on said pivot member whereby pivoting of said second one of said pair of finger members is effective to selectively separate or bring together said pair of finger members.

5. The voluntary opening prehension device as described in claim 1 wherein said electric motor means comprises:
   a direct current micromotor electrically connected to said battery member, said micromotor having a linear shaft extending perpendicularly therefrom at a first end; and
   a cable member connected to said linear shaft member at a first end and attached to one of said finger members at a second end whereby actuation of said direct current micromotor is effective to rotate said shaft member thereby winding said cable member about said shaft, which in turn pivots said finger member into an open position relative to the other of said finger members.

6. The voluntary opening prehension device of claim 1 wherein the threshold detector further comprises hysteresis means for providing hysteresis of the predetermined threshold value thereby preventing the threshold detector from cycling the motor means due to small fluctuations in the myoelectric signal when said myoelectric signal is near the specified minimum voltage strength.

7. The artificial hand of claim 6 wherein the threshold detection means further comprises hysteresis means for providing hysteresis of the predetermined threshold value thereby preventing cycling of the motor means due to small fluctuations in the value of the electrical signal when said value is near the predetermined threshold value.

8. An artificial hand comprising:
an artificial forearm member attachable to the arm of the patient;
a pivot member attached to the distal end of said forearm member;
a pair of finger members extending distally from said pivot member and pivotally mounted thereon, so as to permit selective contact of said finger members to each other proximate their respective distal tips;
electric motor means for selectively separating said finger members;
field effect transistor driver means for actuating said electric motor means when supplied with electrical current;
a battery member for supplying electrical current to said electric motor means;
closing means for urging at least a portion of each of said finger members into contact with each other; and
control means for selectively actuating said electric motor means, said control means including;
an electrode member affixed proximate to a voluntary muscle of the patient for detecting electrical activity generated by actuation of the voluntary muscle of the patient;
a bandpass amplifier electrically connected to said electrode member for amplifying an electrical signal as a result of said electrical activity;
an amplifier electrically connected to said signal detector for rectifying said electrical signal and fur supplying a myopulse to said field effect transistor driver; and,
threshold detection means for comparing the myopulse to a predetermined threshold value and for inhibiting actuation of said electric motor means whenever the myopulse signal has a value less than the predetermined threshold value.

9. The artificial hand as described in claim 8 and further comprising:
socket means for rapid selective attachment or removal of said pivot member to said forearm member.

10. The artificial hand as described in claim 9 and further comprising:
an elastic resilient thermoplastic covering encompassing said finger members and formed in the shape of a hand so as to simulate the appearance and function of a natural hand and to urge said finger members into contact with each other.

11. The artificial hand as disclosed in claim 10 and further comprising:
a second pivot member interchangeably attachable to said socket member, and having a pair of fingers extending distally therefrom and pivotally mounted thereon, so as to provide selective attachment of:
(1) said pivot member with said thermoplastic covering encompassing said finger member or
(2) said socket member as desired.

12. The artificial hand as disclosed in claim 8 and further comprising:
retriggerable timer means for limiting actuation of said electric motor means to a selected time period, so as to reduce the power consumption of said artificial hand member.

13. The artificial hand as disclosed in claim 12 wherein said selected time period is 4 seconds.

14. The prosthetic device as described in claim 12 wherein said desired period of actuation is approximately four seconds, so as to allow time for grasping of an object and at the same time effect conservation of said electrical power.

15. The artificial hand as described in claim 8 wherein said field effect transistor driver comprises:
a vertical metal oxide semiconductor transistor having a voltage of 40–70 millivolts when driving said electric motor means, said vertical metal oxide semiconductor transistor being effective to reduce the voltage drop to said electric motor means and thereby to operate said artificial hand more efficiently.

16. The artificial hand as described in claim 8 wherein said amplifier comprises:
a complimentary metal oxide semiconductor bandpass amplifier.

17. The artificial hand as described in claim 8 wherein said closing means comprises:
an elastic band member connecting said finger members so as to resiliently retain said finger members in contact with each other.

18. The artificial hand as described in claim 8 and further comprising:
a smoothing circuit electrically connected to said signal detector for removing fluctuations in output current; and
a buffer circuit interposed between said amplifier and said electric motor means for electrical isolation of said processor.

19. The artificial hand as described in claim 8 and further comprising:
a thermoplastic covering encompassing said finger members and formed in the shape of a hand so as to simulate the appearance and function of a natural hand.

20. The artificial hand as described in claim 8 wherein said thermoplastic covering is selectively removable by the user.

21. A myoelectrically controller prosthetic device comprising:
a housing member;
means for attaching said housing member to the natural limb of the patient;
an artificial limb member extending distally from said housing member and movably attached thereto;
electric motor means for selective movement of said artificial limb member, relative to said housing member;
a battery member for supplying electrical power to said electric motor means;

control means for selectively actuating said electric motor means, in response to movement of one or more selected voluntary muscles of the patient;

a field effect transistor driver for actuating said electric motor means when a specified threshold signal has been detected from the patient;

said control means including a signal detector for detecting myoelectric signals generated by the user;

a processor for processing said myoelectric signal into a myopulse directed to said field effect transistor driver for actuation thereof; and threshold detection means for comparing the myopulse signal to a predetermined threshold value and for inhibiting actuation of the field effect transistor whenever the myopulse has a value less than the predetermined threshold value.

22. The prosthetic device as described in claim 21 and further comprising:

timer means for deactivating said electric motor means after a desired period of actuation so as to conserve the electrical power of said battery.

23. The prosthetic device as described in claim 21, wherein said prosthetic device utilizes a quiescent current of 18 microamperes or less.

24. The prosthetic device as described in claim 15 wherein said battery means comprises a 9-volt transistor battery.

25. The prosthetic device as described in claim 21 and further comprising an easy access battery chamber for selective removal and replacement of said battery means, as required.

26. The myoelectrically controlled prosthetic device of claim 21 wherein the threshold detector means further comprises hysteresis means for providing hysteresis of the predetermined threshold value thereby preventing cycling of the motor means due to small fluctuations in the value of the myopulse when said value is near the predetermined threshold value.

* * * * *